(12) United States Patent
Myers et al.

(10) Patent No.: US 6,432,635 B1
(45) Date of Patent: Aug. 13, 2002

(54) CYSTATIN B MUTANTS

(75) Inventors: Richard M. Myers, Stanford; David R. Cox, Belmont; Len A. Pennacchio, Menlo Park, all of CA (US); Anna-Elina Lehesjoki, Espoo (FI); Albert De La Chapelle, Helsingfors (FI)

(73) Assignees: Helsinki University Licensing Ltd. Oy, Helsinki (FI); The Board of Trustees of the Leland Stanford Jr. Univeristy, Stanford, CA (US)

( * ) Notice: Subject to any disclaimer, the term of this patent is extended or adjusted under 35 U.S.C. 154(b) by 0 days.

(21) Appl. No.: 08/819,872

(22) Filed: Mar. 18, 1997

Related U.S. Application Data
(60) Provisional application No. 60/013,975, filed on Mar. 21, 1996.

(51) Int. Cl.[7] ................................................. C12Q 1/68
(52) U.S. Cl. ..................... 435/6; 435/810; 436/501; 935/23; 935/78; 935/88; 536/27
(58) Field of Search ..................... 435/6, 810; 436/501; 935/23, 78, 88; 536/27

(56) References Cited

U.S. PATENT DOCUMENTS

| | | | |
|---|---|---|---|
| 5,124,246 A | 6/1992 | Urdea et al. |
| 5,223,409 A | 6/1993 | Ladner et al. |
| 5,270,170 A | 12/1993 | Schatz et al. |
| 5,283,185 A | 2/1994 | Epand et al. |
| 5,288,609 A | 2/1994 | Engelhardt et al. |

OTHER PUBLICATIONS

Abrahamson, M. et al., "The human cystatin C gene (CST3), mutated in hereditary cystain C amyloid angiopathy, is located on chromosome 20," *Hum. Genet.* 82:223–226 (1989).

Appel, J.R. et al., "Elucidation of Discontinuous Linear Determinants in Peptides," *J. Immunology* 144(3): 976–983 (1990).

Berkovic, S.F. et al., "Progressive myoclonus epilepsies: Specific causes and diagnosis," *N. Engl. J. Med.* 315(5):296–305 (1986).

Felgner, P.L. et al., "Lipofection: A highly efficient, lipid–mediated DNA–transfection procedure," *Proc. Natl. Acad. Sci. U.S.A.* 84:7413–7417 (1987).

Ghiso, J. et al., "Amyloid fibrils in hereditary cerebral hemorrhage with amyloidosis of Icelandic type is a variant of γ–trace basec protein (cystatin C)" *Proc. Natl. Acad. Sci. U.S.A.* 83:2974–2978 (1986).

Greenberg, D.A. et al., "Juvenile myoclonic epilepsy (JME) may be linked to the BG and HLA loci on human chromosome 8," *Am. J. Med. Genet.* 31:185–192 (1988).

Ichikawa, H. et al., "A NotI restriction map of the entire long arm of human chromosome 21," *Nature Genetics* 4:361–366 (1993).

Järvinen, M. et al., "Human spleen cysteineproteinase inhibitor," *Biochem Biophys Acta* 708:210–217 (1982).

Jerala, R. et al., "Clonging a synthetic gene for human stefin B and its expression in *E. coli*," *FEB* 239(1):41–44 (1988).

Jerala, R. et al., "Deletion of the carboxy terinal part of stefin B does not have a major effect for binding to papain," *Biomed. Biochim.* 50:627–629 (1991).

Jou, Y.S et al., "Localization of the $\alpha_2$–Macroglobulin Receptor–Associated Protein 1 Gene (LRPAP1) and other Gene Fragments to Human Chromosome 4p16.3 by Direct cDNA Selection," *Genomics* 24:410–413 (1994).

Koskiniemi, M., "Psychological Findings in Progressive Myoclonus Epilepsy Without Lafora Bodies," *Epilepsia* 15:537–545 (1974).

Koskiniemi, M. et al., "Progressive Myoclonus Epilepsy, a clinical and histopathological study," *Acta. Neurol. Scandin.* 50:307–332 (1974).

Koskiniemi, M. et al., "Progressive Myoclonus Epilepsy, electroencephalographical findings," *Acta. Neurol. Scandin.* 50:333–359 (1974).

Lehesjoki, A.E. et al., "Localization of a gene for progressive myoclonus epilepsy to chromosome 21q22," *Proc. Natl. Acad. Sci. U.S.A.* 88:3696–3699 (1991).

Lehesjoki, A.E. et al., "Linkage studies in progressive myoclonus epilepsy: Unverricht–Lundborg and Lafora's diseases," *Neurology* 42:1545–1550 (1992).

Lehesjoki, A.E. et al., "Localization of the EPM1 gene for progressive myoclonus epilepsy on chromosome 21: linkage disequilibrium allows high resolution mapping," *Hum. Mol. Genet.* 2(8) :1229–1234 (1993).

(List continued on next page.)

*Primary Examiner*—W. Gary Jones
*Assistant Examiner*—Janell E. Taylor
(74) *Attorney, Agent, or Firm*—Bret E. Field; Paula A. Borden; Bozicevic, Field & Francis, LLP.

(57) ABSTRACT

An isolated nucleic acid molecule, wherein the molecule contains:

(1) a first sequence consisting of human cystatin B genomic DNA as set forth in FIG. 3 (SEQ ID NO:1);

(2) a second sequence, wherein said second sequence is a subsequence of said first sequence, is at least nucleotides in length, and is not present in human cystatin B cDNA;

(3) a third sequence in which at least one nucleotide of said first or second sequences is replaced by a different nucleotide; or (4) a fourth sequence complementary to any of said first, second or third sequences;

with the proviso that (I) if said molecule is an RNA molecule, U replaces T in said sequence of said molecule, and (ii) said third sequence is at least 95% identical to said first or second sequence.

5 Claims, 5 Drawing Sheets

OTHER PUBLICATIONS

Liu, A.W. et al., "Juvenile Myoclonic Epilepsy Locus in Chromosome 6p21.2–p11: Linkage to Convulsions and Electroencephalography Trait," *Am. J. Hum. Genet.* 57:368–381 (1995).

Lovett, M. et al., "Direct selection: A method for the isolation of cDNAs encoded by large genomic regions," *Proc. Natl. Acad. Sci. U.S.A.* 88:9628–9632 (1991).

Muller, S.R. et al., "Laboratory Methods: Efficient Transfection and Expression of Heterologous Genes in PC12 Cells," *DNA and Cell Biology* 9(3):221–229 (1990).

Norio, R. et al., "Progressive myoclonus epilepsy: genetic and nosological aspects with special reference to 107 Finnish patients," *Clin. Genet.* 15:382–398 (1979).

Pearson, W.R. et al., "Improved tools for biological sequence comparison," *Proc. Natl. Acad. Sci. U.S.A.* 85:2444–2448 (1988).*

Ritonja, A. et al., "Amino Acid Sequence of the Intracellular Cysteine Proteinase Inhibitor Cystatin B from Human Liver," *Biochem. Biophys. Res. Comm.* 131(3):1187–1192 (1985).*

Scheur, M.L. et al., "The Evaluation and Treatment of Seizures," *N. Engl. J. Med.* 323(21):1468–1474 (1990).*

Serratosa, J.M. et al., "The gene for progressive myoclonus epilepsy of the Lafora type maps to chromosome 6q," *Hum. Mol. Genet.* 4(9):1657–1663 (1995).*

Thiele, U. et al., "Gene Synthesis, Expresion and Isolatio nof an inhibitorily Active MS–2 pol–Stefin B Fusion Protein and preparation of Des[Met] stefin B," *Biol. Chem.* 369:1167–1178 (1988).*

Thiele, U. et al., "N–Terminal Variants of Recombinant Stefin B: Effect on Affinity for Papain and Cathepsin B," *Biol. Chem.* 371:125–136 (1990).*

Turk, V. et al., "The cystatins: protein inhibitors of cystein proteinases," *FEBS* 285(2):213–219 (1991).*

* cited by examiner

FIG. 2A
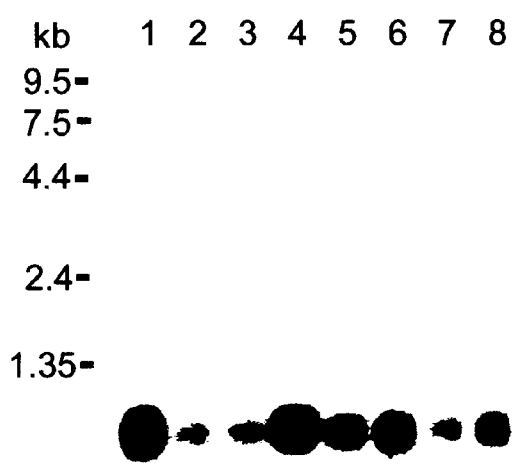
FIG. 2B
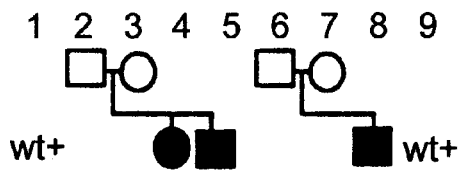
 ← cystatin b
 ← β-actin

```
CTGCAGGATT GCCCCTACTC CGACTGCCCC TTCCCTATCG TCCCACCCTG CGCGCCCAAC    60
CCACCGGCGA CACCCGGCCG CGCCCCCGCC CCGGTCCGTG TGACTCGGCG CCCGGAAAGA   120
CGATACCAGC CCCGGGAGGG GGGCGCTCCC TCCCGACACC AGCGCTGGGC GCGGAGACCC   180
AGCCTGCGGC GAGTGGTGGC CAGGCTCCCC GCCCCGCGCC CCGCCCCGCG CCCCGCCCCG   240
CGCGTCCCTT CTTGCGGGGC CACCGCGACC CCGCAGGGGA CTCCGAAGCC AAAGTGCCTC   300
CTCCCCGCCC CTTGGTTCCG CCCGCGCGTC ACGTGACCCC AGCGCCTACT TGGGCTGAGG   360
                                "5' UTR"
AGCCGCCGCG TCCCCTCGCC GAGTCCCCTC GCCAGATTCC CTCCGTCGCC GCCAAG       416
```

```
ATG ATG TGC GGG GCG CCC TCC GCC ACG CAG CCG GCC ACC GCC GAG ACC     464
Met Met Cys Gly Ala Pro Ser Ala Thr Gln Pro Ala Thr Ala Glu Thr

CAG CAC ATC GCC GAC CAG GTGGGTGGGC CGCGGGGACG GGGCCGGCCC             512
Gln His Ile Ala Asp Gln
```

```
GGAGTCCTGC CTTAGCCTCA GGGCGCGGCC GCGGCTCCTG GAGCGAAAGA AGCCGCTTTG   572
GCCCCGCTGC GCACCCCTGG GCTGGCCCGG GCTGTGGCCG TGAGAGGCCT CCCTCCGCTC   632
GGGTCGCGCG CGAGTGAGCA GCGGGGGGCC GCGCCTGGGG CGCCGCTGGG GAGACATTGG   692
GCTCCGCTGA ATACAGCAAG GGCGAGTGGG AATTGATAGC CCGGAGCAGG GTGCGGTCCC   752
TGCATGGACA GTCTCTGAGA GGAAACCCCA GGGATGAGGC GCTTCTGGTT TCAGGCAGGC   812
AGGGTGATCG GGCGTCGCCG GCGATGGCGC AGGTGAGCAG CCGGCTCCGA TCTCCACGGT   872
GATCCGATAG CAAGCGGGTG GAAGGGTCT GGCTAAACTG ACTTAGCCAG GCTTCTTGCT    932
AAAAGTGGAT TTTACAAGGA AGTGCGCAGG TGGCCTAGGC GCTTCAGGAG CCCGACTACA   992
GTTTGGCCAA GCAAGAATCT TTGTCAATAT CCTCATCTAG TTCGGGAAAA AAATCATGAG  1052
AGAGAGTGCA AGAGGTCCCC AGTGATAAGG CACATGGGTT AAAAACTTAA GTGTATCTGC  1112
ATAAAAGGTC CACAGGTTTC TTTACATGCT TCCGATTCTA GCACTGTTTC AAACTGTAAG  1172
TCTAAATAAA AAGTTAAAAC ACAGAAAAAC AAGATAAAAA CCGGGCTGGG TTGCAGATGG  1232
CAACTTCCCT GTGTCTCGGT TTCCTCGTCT GTAAAATGGA CGTCCTGTTG CTCTGCGCCT  1292
GCCAGAAGAT TCTGGAGGGG CTGAAATGAG CAGGTCATCT GTGCAAGAAG CCCCCTCCGG  1352
TGGAGCACAG GCCAGGCCCG CCTCGCTGTC ATGGTTGGTG ACCGACGGGA TGCCCCAAGC  1412
AAGAACAGGT CCAGGCGATG CTGAGGCCTG TGTTTTTTTT TTTTGTTTTT GAGACTCAGT  1472
CTCAACTCTT GCCCAGGGTG GAGTGCAGTG GCACAATCTC GGCCCACTGC AACCTCCGCT  1532
TCCCAGGTTC AAGGGATTCT CCTGCCTTAG CCTCCCGAGT AGCTGGGATT GCAGGTGCTC  1592
GCCACCACGC CCAGCTAATT TTTGTATTTT TAGTAGAAAC GGGGTTTTGC CATTTGGCTA  1652
GGCTGGTCTC AAACTCCTGA CCTCAAGTGA TCCGCCCACC TCAGCCTCCC AAAGTTCTGG  1712
GATTACATCC TTGAGCCACC GTACCCAGCT GGAACTGTTT TTTTCTACTT TATTATTAGG  1772
CTGACAGTTT AAATGTCCCT TCAGTTGTAA GAGACAATTG TGTGAAGAGC CAGTGTCAGA  1832
```

FIG. 3i

```
ATCGTGTGTG TGCTCACATG CGTGCAAGTT ACTCTAGCAG GAGGGAATCC AAGAAGCCAC 1892
                                        C
TGAGACATCC TCATTCTGTC CCTTCTGTCT AG GTG AGG TCC CAG CTT GAA GAG   1945
                                   Val Arg Ser Gln Leu Glu Glu

AAA GAA AAC AAG AAG TTC CCT GTG TTT AAG GCC GTG TCA TTC AAG AGC   1993
Lys Glu Asn Lys Lys Phe Pro Val Phe Lys Ala Val Ser Phe Lys Ser

CAG GTG GTC GCG GGG ACA AAC TAC TTC ATC AAG GTAGAGTGTG GGCCTCAGGA 2046
Gln Val Val Ala Gly Thr Asn Tyr Phe Ile Lys

GGGCCTGCCC CGAACGGGTG CTGGTAGGAA ACCGCCTGTG CAGGCCCGGG CTGTGTGGTC 2106

TTAGGTGCTG GGGCGCCCTG TGGCTGCCCC CTGAGATAAG CATCCTACTG TGTGTGTCCA 2166

TCGGCCTTTC AGGAGGACTA GGGCTTCTGG GGAGCTAAGA ACCCCAAGGA AACAAGTGTG 2226

GGATGTGAGG CATCCCCTGC ACATGCAGGA GAAGACAAGA TTGTCTTCAG CTGGCTGCTA 2286

ATGACCTGGA GGGGCGCAGC AAGGTGACTT GGGATCAGAG GCTTCGCTCA CTCCGCTCTC 2346
                                                     T
TTCCCAG GTG CAC GTC GGC GAC GAG GAC TTC GTA CAC CTG CGA GTG TTC  2395
        Val His Val Gly Asp Glu Asp Phe Val His Leu Arg Val Phe

CAA TCT CTC CCT CAT GAA AAC AAG CCC TTG ACC TTA TCT AAC TAC CAG  2443
Gln Ser Leu Pro His Glu Asn Lys Pro Leu Thr Leu Ser Asn Tyr Gln

ACC AAC AAA GCC AAG CAT GAT GAG CTG ACC TAT TTC TGATCCTGAC       2489
Thr Asn Lys Ala Lys His Asp Glu Leu Thr Tyr Phe
                                  "3'-UTR"
TTTGGACAAG GCCCTTCAGC CAGAAGACTG ACAAAGTCAT CCTCCGTCTA CCAGAGCGTG 2549

CACTTGTGAT CCTAAAATAA GCTTCATCTC CGCTGTGCCC TTGGGGTGGA AGGGGCAGGA 2609

TTCTGCAGCT GCTTTTGCAT TTCTCTTCCT AAATTTCATT GTGTTGATTT CTTTCCTTCC 2669

CAATAGGTGA TCTTAATTAC TTTCAGAATA TTTTCAAAAT AGATATATTT TTAAAATCCT 2729

TACAGATTGC CTCCTTTGCT TTTAGACTTT TTTCTTGCTG CTAACCACCC CGGGCAGGTC 2789

CTTCCCCTCC AGGCAGGAGG GCGGAGAGAG TC                              2821
```

CYSTATIN B MUTANTS

This application claims the benefit of the priority date of U.S. Ser. No. 60/013,975, filed Mar. 21, 1996, which is incorporated by reference in its entirety.

ACKNOWLEDGMENTS

This invention was supported in part by grants from the National Institute of Health (P50 HG-00206, HG-24610 and NS31831). The U.S. Government may have rights in this invention.

BACKGROUND OF THE INVENTION

This invention is directed to a genetic sequence that has been identified as the locus of mutations that cause epilepsy and to methods for the diagnosis of this disease and for the detection of the presence of the mutated gene as an indication of potential for genetic transmission of a disease.

BACKGROUND

Cystatin B is a small protein that is a member of a superfamily of cysteine protease inhibitors, which are generally grouped into three families based on structural relationships—stefins (of which cystatin B is a member), cystatins and kininogens (Jarvinen, M. et al., *Biochim. Biophys. Acta* 708:210–217 (1982); Turk, V. et al., *FEBS Lett* 285:213–219 (1991)). It is a tightly-binding reversible inhibitor of cathepsins L, H and B, is found in all tissues, and is thought to inactivate proteases that leak out of the lysosome (Jarvinen, M. et al., (1982); Turk, V. et al., (1991); Ritonja, A. et al., *Biochem. Biophys. Res. Commun.* 131:1187–1192 (1985); Jerala, R. et al., *FEBS Lett* 239:41–44 (1988)). Its amino acid sequence in humans is known (Jarvinen, M. et al., (1982); Turk, V. et al., (1991)). Another member of this family of protease inhibitors, cystatin C, has been shown to be responsible for hereditary cerebral amyloid angiopathy (Abrahamson, M. et al., *Hum. Genet.* 82:223–226 (1989); Ghiso, J. et al., *Proc. Natl. Acad. Sci. U.S.A.* 83:2974–2978 (1986)). This dominantly-inherited disease is characterized by the deposition of cystatin C-rich amyloid fibrils in affected brain arteries.

Progressive myoclonus epilepsy refers to a heterogeneous group of severe inherited epilepsies that are characterized by myoclonic seizures, generalized epilepsy and progressive neurological deterioration, including dementia and ataxia (Berkovic, S. F. et al., *N. Enql. J. Med.* 315:296–305 (1986)). One of the five recognized members of this class is progressive myoclonus epilepsy of the Unverricht-Lundborg type (EPM1; H. Unverricht, *Die Myoclonie* (Franz Deuticke, Vienna), pp. 1–128 (1891); H. Unverricht, *Disch, Z. Nervenheilk* 7:32–67 (1895); H. Lundborg, Die Proqressive Mvoclonus-Epilepsie (*Unverrichts Myoklonie*) Almquist & Wiksell, Uppsala, pp. 1–207 (1903). This form of epilepsy is inherited as an autosomal recessive disease in which patients have severe stimulus-sensitive myoclonus and tonic-clonic seizures beginning between ages 6 and 15, and have a variable rate of progression between and within families (Koskiniemi, M., *Epilepsia* 15:537–545 (1974); Koskiniemi, M. et al., *Acta Neurol. Scandinav.* 50:333–359 (1974); Koskiniemi, M. et al., *Acta Neurol. Scandinav.* 5:307–332 (1974); Norio, R. et al., *Clin Genet.* 15:382–384 (1979)). Seizures tend to diminish at 25–30 years of age, although mild dementia generally develops late in the course of the disease. Unlike the other progressive myoclonus epilepsies, inclusion bodies or storage material are not observed in EPM1, and diagnosis of the disease is usually based on clinical history, typical electroencephalographic abnormalities, and the exclusion of the other four subtypes (Lafora's disease, MERRF syndrome, neuronal ceroid lipofuscinosis and sialidosis); EPM1 and other forms of epilepsy affect about 3% of the world's population (Scheuer, M. L. et al., *N. Enql. J. Med.* 323:1468–1474 (1990)).

The genes responsible for Lafora's disease and juvenile myoclonus epilepsy, which have symptoms similar to EPM1, have been localized to specific chromosomal regions by meiotic linkage analysis (Serratosa, J. M. et al., *Hum. Mol. Genet.* 4:1657–1663 (1995); Greenberg, D. A. et al., *Am. J. Med. Genet.* 31:185–192 (1988); Liu, A. W. et al., *Am. J. Hum. Genet.* 57:68–381 (1995)). Linkage analysis initially localized the gene responsible for EPM1 to a 2 million base pair (Mb) region on the long arm of human chromosome 21 between the DNA markers CBS and CD18 (Lehesjoki, A. E. et al., *Proc. Natl. Acad. Sci. U.S.A.* 883696–3699 (1991); Lehesjoki, A. E. et al. Neurolocv 42:1545–1550 (1992); Lehesjoki, A. E. et al., *Hum. Molec. Genet.* 2:1229–1234 (1993)). However, prior to the current elucidation of a molecular defect for cystatin B, no specific defects have been found to be associated with EPM1.

SUMMARY OF THE INVENTION

One aspect of the invention is an isolated nucleic acid molecule, wherein said molecule comprises:

(1) a first sequence consisting of human cystatin B genomic DNA as set forth in FIG. 3 (SEQ ID NO:1);

(2) a second sequence, wherein said second sequence is a subsequence of said first sequence, is at least 10 nucleotides in length, and is not present in human cystatin B cDNA;

(3) a third sequence in which at least one nucleotide of said first or second sequences is replaced by a different nucleotide; or (4) a fourth sequence complementary to any of said first, second or third sequences;

with the proviso that (I) if said molecule is an RNA molecule, U replaces T in said sequence of said molecule, and (ii) said third sequence is at least 95% identical to said first or second sequence.

Another aspect of the invention is an isolated nucleic acid molecule, wherein said molecule comprises a first sequence in which at least one nucleotide of cystatin B cDNA is replaced by a different nucleotide or a second sequence complementary to said first sequence, with the proviso that (I) if said molecule is an RNA molecule, U replaces T in said sequence of said molecule and (ii) said first sequence is at least 95% identical to cystatin B cDNA.

Another aspect of the invention is a method of detecting the presence of a genetic defect that causes epilepsy in a human or that can transmit epilepsy to an offspring of said human which comprises:

identifying a mutation of a cystatin B gene of said human, wherein said mutation provides a cystatin B gene sequence different from human cystatin B genomic DNA sequence as set forth in FIG. 3 (SEQ ID NO:1).

Another aspect of the invention is a method for treating an individual with progressive myoclonus epilepsy, comprising supplying to said individual an effective amount of a gene product of a cystatin B gene.

BRIEF DESCRIPTION OF THE DRAWINGS

The invention now being generally described, the same will be better understood by reference to the following detailed description of specific embodiments in combination with the figures that form part of this specification, wherein:

FIG. 2 is a schematic drawing depicting mRNA analysis of the cystatin B gene in affected and unaffected individuals. (A) A cystatin B cDNA probe (approx. 500 bp) was hybridized to RNA blots. Each lane contained 2 μg of polyadenylated mRNA from eight human tissues (Clontech, Palo Alto, Calif.) including: 1, heart; 2, brain; 3, placenta; 4, lung; 5, liver; 6, skeletal muscle; 7, kidney; and 8, pancreas. The size of the cystatin B mRNA is less than 1 kb, consistent with the 642 bp of the original full-length cDNA sequence described in (Ritonja et al. (1985)). (B) The same probe was hybridized to RNA blots containing 20 μg of total RNA from lymphoblastoid cell lines (upper panel). 1 and 9, unaffected non-carrier controls; 2–5 are from a Finnish family with EPM1, including: 2, carrier father; 3, carrier mother; 4, affected child; 5, affected child. 6–8 are from an American family, including: 6, carrier father, 7, carrier, mother; 8, affected child. A human β-actin probe was hybridized to the same Northern blot to assess the approximate quantity of RNA loaded per lane (lower panel).

FIG. 3 depicts the genomic sequence of the human cystatin B gene (SEQ ID NO:1). The mature mRNA transcript starts at position 322 and extends to position 2732. Amino acids in the cystatin B protein are designated below the nucleotide sequence (Ritonja et al. (1985)) (SEQ ID NOS:1–2). Underlined bases designate potential Sp1 binding sites in the 5' flanking region. 5' and 3' untranslated regions are indicated by 5' UTR and 3' UTR, respectively. The two mutations we identified in this study are designated by boxes, where the mutant sequence is shown above the wild-type sequence.

The 2,500 bp sequence of the cystatin B gene was determined as follows. We first determined that the entire gene is present on a 9 kb EcoRI fragment in several genomic clones from a cosmid and BAC contig of the region. Oligonucleotide primers based on the cDNA sequence were used to determine the sequences of the exon/intron junctions, and additional primers were generated on the basis of this information to determine the complete sequence of the gene, which has been deposited in GenBank (U46692).

Figure 4A:
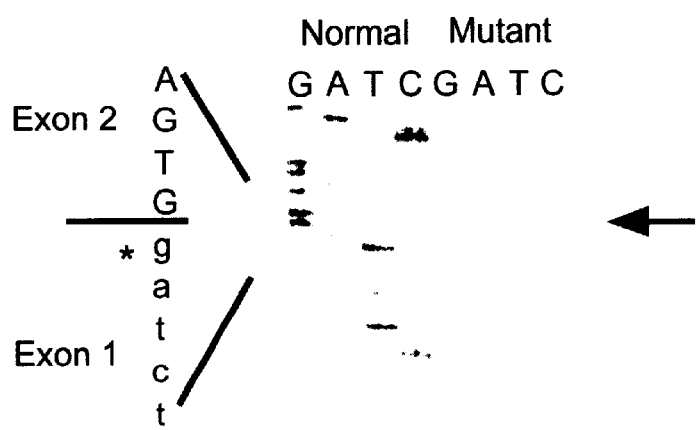

FIG. 4 depicts DNA sequence analysis of the cystatin B gene in EPM1 patients. (A) A portion of an autoradiogram showing the DNA sequence of cloned PCR products from and unaffected chromosome (left panel) and an affected chromosome from an American family (right panel), both of which we had transferred into somatic cell hybrids to allow single alleles to be separately analyzed. Amplification primers were designed on the basis of the cystatin B genomic sequence to produce 803 bp products (primers F11, R1), which were cloned into a plasmid vector. Ten independent clones were sequenced with primer F11, all of which produced the mutant sequence shown in the right panel. This transversion mutation changes the last nucleotide of the 3' splice acceptor of intron 1 from a G to a C in the affected chromosome, as noted by the arrow and asterisk. (B) A portion of an autoradiogram showing the nucleotide sequence determined directly from amplified PCR products from an unaffected chromosome (left panel) and an affected chromosome from a Finnish family (right panel). The PCR products were excised from agarose gels and purified by Gene-Clean (Bio-101) prior to sequencing. The asterisk and arrow indicate the C to T transition mutation in this patient that results in the formation of a stop codon in the cystatin B coding sequence. Because the affected individual is a heterozygous for the stop codon mutation, two bands are seen at this position in the autoradiogram. (C) A restriction enzyme screen for the 3' splice site mutation. This mutation destroys a site for the restriction enzyme BfaI. To screen large numbers of genomic DNA samples, 100 ng of genomic DNA was amplified with 20 pmol of primers F11 and R10 with the same conditions we used to amplify the 3' segment of the cystatin B gene for sequencing. The 474 bp product was digested with 10 units of Bfa for 3 hours and the fragments were resolved by electrophoresis in a 2% agarose gel and visualized by ethidium bromide staining. PCR products from an unaffected chromosome result in DNA fragments 260, 140, 53, and 21 bp in length, whereas PCR products from individuals heterozygous for this mutation result in the generation of an additional fragment 313 bp in length due to the loss of a BfaI site separating the 260 bp and 53 bp fragments. Contents of the lanes are as follows: 1 and 7, DNA size markers (1 kb ladder; BRL, Gaithersberg, MD); 2, undigested 474 bp PCR product; 3, BfaI-digested PCR product from and unaffected individual; 4, BfaI-digested PCR product from the father of an EPM1 patient; 5, BfaI-digested PCR product from the mother of the same EPM1 patient; 6, BfaI-digested PCR product from an EPM1 patient, the child of the parents analyzed in lanes 4 and 5. The mother carries the allele of the cystatin B gene that contains the 3' splice mutation, whereas the father carries a different mutant allele.

DESCRIPTION OF THE PREFERRED EMBODIMENT

In its broadest aspect, the present invention is directed to defective protease inhibitors and proteases which result in epilepsy when present in an affected individual. In particular, the protease inhibitors are members of the cystatin superfamily. The present invention arose in the context of investigations based on localizing the gene responsible for EPM1 to a 2,000,000 base pair (Mb) region on the long arm of human chromosome 21 between DNA markers CBS and CD18. The genomic DNA sequence for cystatin B is provided and defects (mutations) in the cystatin B gene have been determined to be responsible for an inherited form of epilepsy called progressive myoclonus epilepsy of the Unverricht-Lundborg type (EPM1). We determined that cystatin B messenger RNA levels were decreased several-fold in cells from patients with the disease compared to cells from unaffected individuals. The identification of the biochemical defect that causes EPM1 provides a basis for treatment of this disease. In addition, knowledge that mutation in the cystatin B gene are responsible for the disease allows mutation detection tests to be used as a definitive diagnosis for this form of epilepsy. Similarly, the methods described herein can be utilized to correlate other forms of epilepsies with defective protease inhibitors and proteases, in particular, with defective protease inhibitors of the cystatin superfamily, thus providing new methods of diagnosis and treatment for these particular epilepsies.

Thus, the present invention provides an isolated nucleic acid molecule, in which the molecule contains (1) a first sequence consisting of cystatin B genomic DNA, as set forth in FIG. 3 (SEQ ID NO:1); (2) a second sequence wherein the second sequence is a subsequence of the first sequence, at least 10 nucleotides in length and is not present in human cystatin B cDNA; (3) a third sequence in which at least one nucleotide of the first or second sequence is replaced by a different nucleotide; or (4) a fourth sequence complementary to any of the first, second, or third sequences; with the provisos that (1) if the molecule is an RNA molecule, U replaces T in the sequence of the molecule, and (2) the third sequence is at least 95% identical to the first or second sequence. Any of these sequences can be used in the identification of the presence (or absence) of a mutation in the cystatin B gene of a human and thus can be used in the diagnosis of epilepsy, in particular, progressive myoclonus epilepsy of the Unverricht-Lundborg type (EPM1) or in the genetic counseling of individuals, for example those with a family history of epilepsy (although the general population can be screened as well). In particular, it should be noted that the invention is not limited to use or identification of the specific mutations that have already been identified. Any mutation in the cystatin B gene away from the normal gene sequence identified here is an indication of a potential genetic flaw, even so-called "silent" mutations that do not encode a different amino acid at the location of the mutation are potential disease mutations, since such mutations can introduce into (or remove from) the gene an untranslated genetic signal that interferes with the transcription or translation of the gene. Since one of the utilities based on the gene sequences identified here is in genetic counseling of families with a history of epilepsy, advice can be given to a patient concerning the potential for transmission of epilepsy if any mutation of the cystatin B gene is present. While an offspring with the mutation in question may or may not have symptoms of epilepsy, patient care and monitoring can be selected that will be appropriate for the potential presence of the disease; such additional care and/or monitoring can be eliminated (along with the concurrent costs) if there are no differences from the normal gene sequence. As additional information (if any) becomes available (e.g., that a given silent mutation or conservative replacement mutation does or does not result in epilepsy), the advice given for a particular mutation may change. However, the change in advice does not alter the initial determination of the presence of absence of mutation in the cystatin B gene that this invention has for the first time indicated to be a sufficient cause of epilepsy.

Molecules containing the full-length cystatin B genomic sequence (SEQ ID NO:1) are useful as sources of subsequences (discussed below) or as starting materials for the preparation of the cystatin B molecule itself. A "subsequence" is a group of consecutive nucleotides from the genomic or cDNA sequences. Such subsequences can be prepared by chemical synthesis from starting nucleotides (as in an automated gene synthesizer) or by biochemical manipulation of the full-length sequences (e.g., using restriction endonucleases to prepare fragments, optionally followed by (1) cleavage of terminal nucleotides with exonucleases and/or (2) size sorting and/or affinity capture to select the desired sequence). Any subsequence of the cystatin B genomic sequence (SEQ ID NO:1) of sufficient length to be unique under the conditions being used is useful as one of the two primers used in a polymerase chain reaction (PCR) amplification of all or part of the genomic cystatin B gene as part of a method of identifying the presence of absence of a given cystatin B gene mutation, such as those described in this specification; the second primer is simply selected from the opposite strand sequence so that the mutation or other sequence to be amplified lies between the two primers.

The length of a subsequence necessary to hybridize uniquely with the desired target sequence will vary with the particular method being used and is within the ordinary skill of those who carry out routine identification of genetic material. Typical primers are at least 10, preferably at least 18, more preferably at least 20 nucleotides in length and typically no more than 200, preferably no more than 100, more preferably no more than 70, even more preferably no more than 50 nucleotides in length.

In addition to those molecules than contain sequences and subsequences identical to those of the cystatin B gene, molecules containing mutated sequences are also useful, as they can be used as specific probes in allele-specific hybridization techniques to detect the presence of specific mutations. Although the discussion below is primarily involved with nucleotide replacement mutations, insertion or deletion of one or more nucleotides in the cystatin B gene are also possible as would be apparent to the artisan in light of the teaching herein. For example, a mutation of an amino-acid-encoding codon into a stop codon (i.e. nonsense mutations) is identified in the following examples; e.g., $Arg^{68} \rightarrow Stop$ (SEQ ID NO:11). (Here and elsewhere in this specification "codon" refers to a nucleic acid triplet in the reading frame of the gene, unless otherwise clear from the context.) Thus, a preferred class of mutant-sequence molecules is one that contains a replacement (or more than one replacement) of a nucleotide that converts a codon to a stop codon at a location other than the 3' terminus of the coding sequence, so that a truncated, non-functional cystatin B polypeptide molecule is encoded. A further preferred class of mutant-sequence molecules is one that contains a replacement (or more than one replacement) of a nucleotide that impairs splicing at the intron-exon boundaries. For example, a G→C mutation in a 3' splice acceptor site in the first intron of the cystatin B gene (SEQ ID NO:10) is described in the examples below. Other preferred classes of mutant-sequence molecules are those known to produce non-functional cystatin B molecules, such as those resulting in non-conservative amino acid replacement, and those that alter translation or transcription signal sequences present in the gene or that introduce improper translation or transcription signal sequences.

It will be recognized that the discussion immediately above refers to sequences and subsequences in the sense strand of genomic DNA. Such sequences can be used to detect the presence of the anti-sense strand of genomic DNA as a result of their complementary nature. However, it is also possible to use a sequence complementary to any of those discussed above, since they will be complementary to and detect the sense strand.

Molecules of the invention will contain a sequence that is different from the human cystatin B cDNA sequence and at least 95% identical to the human cystatin B genomic sequence (SEQ ID NO:1). By 95% identical is meant that the sequence in question contains no more than 5% different nucleotides from the sequence to which it is being compared, counting each insertion, deletion, or substitution of a nucleotide as a single difference. It will be apparent that a sequence less than 20 nucleotides in length will have to be identical to the standard sequence if it is to be greater than 95% identical.

Identity and relative identity can readily be understood by reference to the following examples. For example, if the hypothetical sequence.

abcdabcdabcdabcdabcdabcdabcdabcdabcd which is 40 "nucleotides" in length, is considered to be the standard against which a measurement is being made, each of the following hypothetical nucleotide sequences is 95% identical to the standard sequence (i.e., each has two single nucleotide differences from the standard 40 nucleotide sequence):

abcdabcdabcdabcdabcdabcdabcdabcdab [two deletions at 3' terminus];

abcabcdabcdabcdabcabcdabcdabcdabcdabcd [two random-location deletions];

ababcdabcdabcdabcdabcdabcdabcdabcdabcd [two insertions at 5' terminus];

abcdabcdabcdabdabcdabcdabcdabcdaabcdabcd [one random insertion and one random deletion];

abcdabcdbbcdabcdabcdabcdabcdabcdbbcdabcd [replacement of two "a" nucleotides by "b" nucleotides]; and abcdabcbabcdabcdabcdabcdabcadabcdabcdabcd [one replacement and one insertion].

It will be apparent that many similar examples could be given, particularly with molecules of the invention, which are often of larger size than these examples. However, these examples should suffice to teach a person of ordinary skill the meaning of "% different" as used herein. It will also be readily recognized that the sequences to be compared will be aligned for maximum identity before differences are calculated; while computer programs (such as the FASTA program, described in Pearson, W. R. et al., *Proc. Natl. Acad. Sci. U.S.A.* 85:2444–2448 1988)) can be used, the high degree of required identity means that visual sequence comparison will readily find the maximum homology alignment.

The specific sequences indicated above to be derived from or otherwise related to a cystatin B gene can be the entire sequence of a polynucleotide or can be part of a larger sequence. For example, sandwich hybridization assays that utilize lone polynucleotide sequences containing subsequences that hybridize with different molecules (such as target genomic sequences or sequences present in a second polynucleotide that acts as an anchor to a solid surface) are well known. See, for example, U.S. Pat. Nos. 5,288,609 and 5,124,246.

The word "isolated" when used to refer to a polynucleotide molecule characterized by the sequences set forth in this specification, means separated from at least some of the genomic DNA normally associated with the cystatin B gene and preferably separated from all human cellular materials other than polynucleotides. Gene libraries that may have contained a vector containing an unidentified segment of genomic DNA including the cystatin B gene are not "isolated," as the cystatin B gene was not known to be present and/or was not separated from vectors containing other human DNA. In most cases, an isolated molecule of the invention will have a length of less than 50 kb, preferably less than 30 kb, more preferably less than 20 kb. Minimum lengths have been previously discussed.

Generally, the compositions of the invention will be used in a method of detecting the presence of a genetic defect that causes or may cause epilepsy, in particular EPM1 in a human or that can or may transmit epilepsy to an offspring of the human, in which the compositions are used to identify a mutation of a cystatin B gene of the human. Initially, the practitioner will be looking simply for differences from the cystatin B gene sequence (SEQ ID NO:1) now identified as being normal and not associated with disease, since any deviation from this sequence has the potential of causing disease, which is a sufficient basis for initial diagnosis, particularly if the different (but still unconfirmed) gene is found in a person with a family history of epilepsy. As specific mutations are identified as being positively correlated with EPM1 (or its absence), practitioners will in some cases focus on identifying one or more specific mutations of the cystatin B gene that changes the sequence of a protein product of the cystatin B gene or that results in the cystatin B gene not being transcribed or translated. However, simple identification of the presence or absence of any mutation in the cystatin B gene of a patient will continue to be a viable part of genetic analysis for diagnosis, therapy and counseling.

The actual technique used to identify the cystatin B gene or a cystatin B gene mutant is not itself part of the practice of the invention. Any of the many techniques to identify gene mutations, whether now known or later developed, can be used, such as direct sequencing of the gene from affected individuals, hybridization with specific probes, which includes the technique known as allele-specific oligonucleotide hybridization, either without amplification or after amplification of the region being detected, such as by PCR. Other analysis techniques include single-strand conformation polymorphism (SSCP), restriction fragment length polymorphism (RFLP), enzymatic mismatch cleavage techniques and transcription/translation analysis. All of these techniques are described in a number of patents and other publications; see, for example, *Laboratory Protocols for Mutation Detection*, Landegrun, U., ed., Oxford University Press (1996).

Depending on the patient being tested, different identification techniques can be selected to achieve particularly advantageous results. For example, for a group of patients known to be associated with particular mutations of the cystatin B gene, oligonucleotide ligation assays, "minisequencing" or allele-specific oligonucleotide (ASO) hybridization can be used. For screening of individuals who are not known to be associated with a particular mutations, single-strand conformation polymorphism, total sequence of genetic and/or cDNA and comparison with standard sequences, such as those shown herein, are preferred.

In many identification techniques, some amplification of the host genomic DNA (or of messenger RNA) will take place to provide for greater sensitivity of analysis. In such cases it is not necessary to amplify the entire cystatin B gene, merely the part of the gene or the specific locations within the gene that is being detected. Thus, the method of the invention generally comprises amplification (such as via PCR) of at least a segment of the cystatin B gene, with the segment being selected for the particular analysis being conducted by the diagnostician.

Since EPM1 is an autosomal recessive genetic disease, the method of the invention in some cases will classify the patient as homozygous for the normal cystatin B gene or for the mutated cystatin B gene or heterozygous fro the normal cystatin B gene and the mutated B gene, since this information is informative for genetic counseling.

The patient on whom diagnosis is being carried out can be an adult, as is usually the case for genetic counseling, or a newborn, or prenatal diagnosis can be carried out on a fetus. Blood samples are usually used for genetic analysis of adults or newborns (e.g., screening of dried blood on filter paper), while samples for prenatal diagnosis are usually obtained by amniocentesis or chorionic villus biopsy.

The full-length normal cystatin B genes from humans, as well as shorter genes that produce functional cystatin B proteins, can be used to correct EPM1 in a human patient by supplying to the human an effective amount of a gene product of a human cystatin B gene, either by gene therapy or by in vitro production of the cystatin B protein followed by administration of the protein. Since EPM1 is recessive and is thus treatable by a supplementary supply of cystatin B, such treatment is readily accessible. It should be recognized that the various techniques for administering genetic materials or gene products are well known and are not themselves part of the invention. The invention merely involves supplying the genetic materials or proteins for the invention in place of the genetic materials or proteins previously administered. For example, techniques for transforming cells to produce gene products are described in U.S. Pat. No. 5,283,185 entitled "Method for Delivering Nucleic Acid into Cells," as well as in numerous scientific articles, such as Felgner et al., "Lipofection: A Highly Efficient, Lipid-Mediated DNA-Transfection Procedure," *Proc. Natl. Acad. Sci. U.S.A.* 84:7413–7417 (1987); techniques for in vivo protein production are described in, for example, Mueller et al., "Laboratory Methods—Efficient Transfection and Expression of Heterologous Genes in PC12 Cells," *DNA and Cell Biol.* 9(3):221–229 (1990).

Alternatively, samples selected from libraries of compounds are screened for small molecules that inhibit the protease, for example by mimicking the protease inhibitor. For example, individual compound libraries, natural compound libraries, combinatorial libraries (biological or chemical) e.g., peptide display libraries, etc. or the products of custom synthesis can be screened. These methods, for example, include synthetic peptide libraries, whereby an amino acid at a given position within a peptide of known sequence is varied sequentially during synthesis or chemically modified (Appel., J. R. et al.,*J. Immunol.* 144:976–983 (1990)). Alternatively, recombinant peptide libraries are generated, for example, by using partially random oligonucleotides based on the nucleic acid sequences encoding cystatin B, thereby producing related peptides upon expression which exhibit protease-inhibitory activity. The generation and screening of such peptide libraries are described in U.S. Pat. Nos. 5,223,409 and 5,270,170. Such small molecules that inhibit the protease can then be administered to a human patient in an effective amount to correct EPM1.

Administration of proteins and other molecules to overcome a deficiency disease is well known (e.g., administration of insulin to correct for high blood sugar in diabetes) that further discussion of this technique is not necessary. Some modification of existing techniques may be required for particular applications, but those modifications are within the skill level of the ordinary practitioner using existing knowledge and the guidance provided in this specification.

The invention now being generally described, the same will be better understood by reference to the following detailed examples, which are provided for purposes of illustration only and are not to be considered limiting of the invention.

EXAMPLES

Example 1

The Localization and Cloning of the Cystatin B Gene

Figure 1:
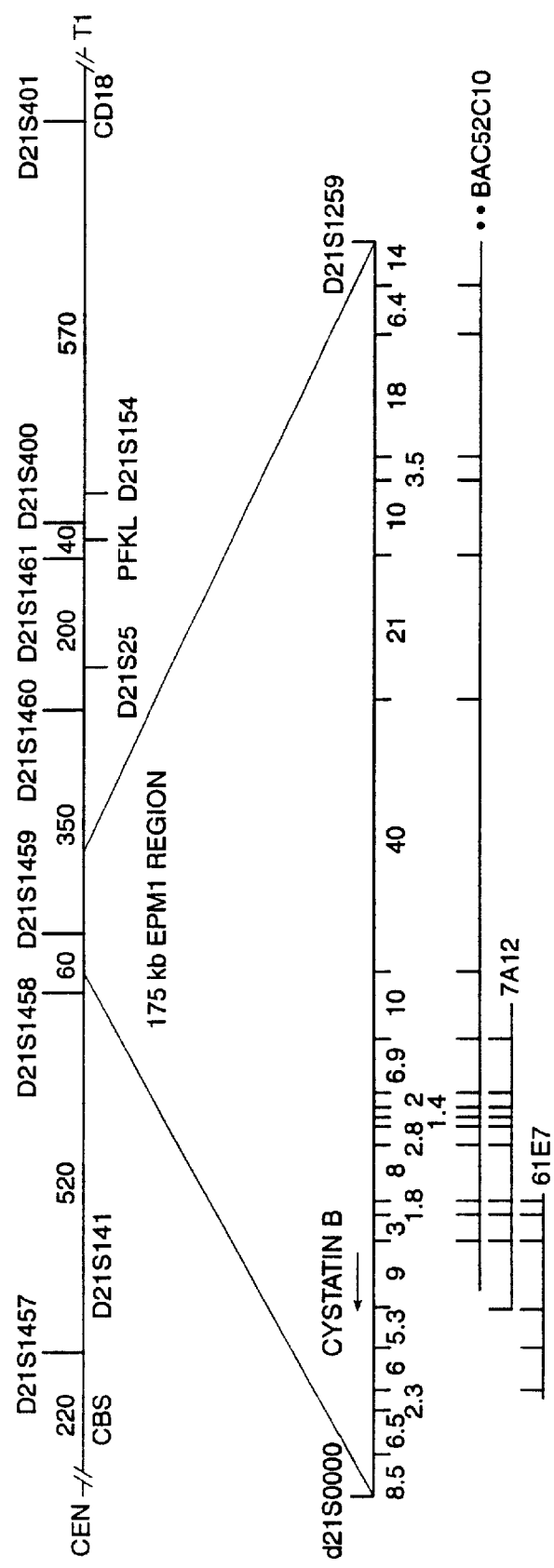
FIG. 1 is a schematic diagram showing physical and genetic mapping information used in the positional cloning of the progressive myoclonus epilepsy (EPM1) gene. The top portion shows a map of the EPM1 region on chromosome 21q22.3, oriented from left to right in the centromeric to telomeric direction, and the numbers above the horizontal line indicate the sizes of the NotI restriction fragments determined by pulsed-field gel electrophoresis (Ichikawa, H. et al., Nat. Genet. 4:361–366 (1992)). The lower portion shows and expansion of the 175 kb segment that refines the location of the EPM1 gene based on genetic mapping and linkage disequilibrium studies. Vertical tickmarks on the expanded region indicate EcoRI restriction sites, with the numbers below indicating the sizes of the restriction fragments. A bacterial artificial chromosome clone (BAC 52C10), which was used as the genomic source for direct cDNA selection, is shown below the EcoRI map, and two cosmid clones (7A12 and 61E7) that contain the cystatin B gene are also depicted. The leftward arrow indicates the location and transcriptional orientation, from 5' to 3', of the cystatin B gene, which is completely encompassed in a 9kb EcoRI restriction fragment, on the chromosome.

Founder effects and bottlenecks in the Finnish population history allowed the use of linkage disequilibrium and recombination breakpoint mapping with Finnish EPM1 patients to refine the location of the EPM1 gene to a region between D21S2040 and D21S1259 (FIG. 1). This region is entirely encompassed in a 750 kilobase pair (kb) bacterial clone contig we generated by STS-content mapping and walking. On the basis of a detailed restriction map of the contig, we determined that the distance between the two DNA markers defining the boundaries of EPM1 is approximately 175 kb. We used this combination of genetic and physical mapping information, as well as the clone reagents, to perform a systematic search for the EPM1 gene.

Direct cDNA selection was used to isolate segments of expressed DNA from the 175 kb region (Lovett, M. et al., *Proc. Natl. Acad. Sci. U.S.A.* 88:9628–9632 (1991); Jou, Y. S. et al., *Genomics* 24:410–413 (1994)). By using bacterial artificial chromosome (BAC) clone 52C10 (commercially available from Research Genetics Inc. Huntsville, Alabama). A group of cDNAs were identified which encode a previously-described protein, cystatin B, a cysteine protease inhibitor (FIG. 1; Jarvinen et al. (1982); Turk et al., (1991)). Hybridization and PCR-amplification experiments indicated that these cDNA segments were derived from a 9 kb EcoRI restriction fragment present in the BAC clone and all the overlapping cosmid clones that were used to build the contig (FIG. 1). These results indicated that the cystatin B gene, which had previously not been mapped to a human chromosome, lies in this segment of human chromosome 21. Further analysis involving multiple restriction digestions and hybridizations demonstrated that the gene is oriented 5' to 3' from the telomere to centromere direction.

Example 2

Expression of Cystatin B Gene in Affected and Unaffected EPM1 Individuals

The cystatin B gene is widely expressed in many cell types as demonstrated by a probe made from the cDNA clone (corresponding to a cDNA sequence starting at position 434 and ending and position 2618 of FIG. 1 (SEQ ID NO:1)) which detects a large amount of mRNA approximately 0.8 kb in length in all tissues examined (FIG. 2A). Measurement of mRNA levels in lymphoblastoid cell lines was used as an initial screen for alteration sin the cystatin B gene in affected individuals. The cell lines were prepared by drawing blood from individuals, transforming the lymphoblasts with EBV and growing the immortalized cells in culture. Total RNA and DNA was extracted from the cultured human lymphoblastoid cell lines. Norther blot hybridization was in 5×SSPE (p.9 M NaCl, 50mM $NaH_aPO_4pH$ 7.4, 5.0 mM EDTA), 10×Denhardt's solutions, 100 $\mu g/ml$ salmon sperm DNA, 50% formamide, and 2% SDS at 42° C. for 18 hours. Filters were washed with 2×saline sodium citrate (SSC) at room temperature for 30 minutes and in 0.1×SSC at 60° C. for 30 minutes. On Northern blots, lymphoblastoid cells from affected individuals from a Finnish family (FIG. 2B, lanes 4–5), an American family (FIG. 2B, lane 8), and two other families had dramatically reduced cystatin B mRNA levels compared to levels from an unaffected, non-carrier individual (FIG. 2B, lanes 1 and 9) and carrier parents of EPM1 patients (FIG. 2B, lanes 2–3 and 6–7) suggesting that the cystatin B gene on the chromosomes from these affected individuals is mutated in a manner that results in decreased levels of mature mRNA, and that these mutations play a primary role in EPM1.

Example 3

Mutations in the Cystatin B Gene in EPM1

The cystatin B gene from an affected individual from each of the four EPM1 families in this study was sequenced. Because only cDNA and not genomic sequence information from the human gene was available, we first determined the entire nucleotide sequence of the human gene that we isolated from an unaffected chromosome (FIG. 3). This sequencing revealed that the gene is 2,500 base pairs (bp) in length and contains three small exons encoding the 98 amino acid cystatin B protein, whose mature mRNA and amino acid sequence were previously known (Ritonja et al. (1985)). The GenBank number for the genomic sequence determined in this study was U46692. Abbreviations for amino acids residues are A, Ala; C, Cys; D, Asp; E, Glu; F, Phe; G, Gly; H, His; I, Ile; K, Lys; L, Leu; M, Met; N, Asn; P, Pro; Q, Gln; r, Arg; S, Ser; T, Thr; V, Val; W, Trp; and Y, Tyr. The GenBank number for the cDNA sequence, deposited by K. S. Bhat, is L03558.

Based on this information, we used the polymerase chain reaction (PCR) to amplify the cystatin B gene and determined its sequence from affected individuals in four different families.

The cystatin B gene was PCR-amplified in two overlapping segments from genomic DNA of affected individuals. These included a 5' segment with oligonucleotide primers pF2 and 51814R1 and a 3' segment with primers F11 and R1.

(pf2: 5'-CTCCGACTGCCCCTTCCCTAT-3' (SEQ ID NO:3);

51814R1: 5'-GAGACACAGGGAAAGTTGCCATCT-3' (SEQ ID NO:4);

F11: 5'-CCACCGTACCCAGCTGGAACTGT-3' (SEQ ID NO:5);

R1: 5'-CGGAGGATGACTTTGTCAGTCTTC-3' (SEQ ID NO:6). These primers were used for PCR-amplification and for sequencing.

The following primers were also used for sequencing:

F3: 5'-TAAGGCCGTGTCATTCAAGAGCCA-3' (SEQ ID NO:7);

F5: 5'-CGCCGAGACCCAGCACATC-3' (SEQ ID NO:8);

R10: 5'-TCTTAGCTCCCCAGAAGCCCTAGT-3' (SEQ ID NO:9). The PCR assay for the 5' segment of the gene included 10% dimethylsulfoxide (DMSO) and 50% deaza-dGTP and the following cycling conditions: Initial incubation at 95° C. for 5 minutes followed by 30 cycles of 30 seconds at 95° C., 30 seconds at 65° C., 30 seconds at 65° C., 2 minutes at 72° C., with a final incubation for 10 minutes at 72° C. Conditions for amplifying the 3' segment of the gene included an initial incubation at 94° C., 30 seconds at 60° C., 2 minutes at 72° C., with a final incubation for 10 minutes at 72° C. PCR products were purified with a Centricon-100 concentrator (Micon; Beverly, Mass.) and sequenced directly by using cycle sequencing with SequiTherm DNA polymerase (Epicentre; Madison, Wis.) or cloned into a plasmid vector. Cloned products were manually sequenced with Sequenase (United States Biochemicals, Cleveland, Ohio). The sequencing reaction products were separated on 6% polyacrylamide gels and visualized by autoradiography.

Figure 4B:
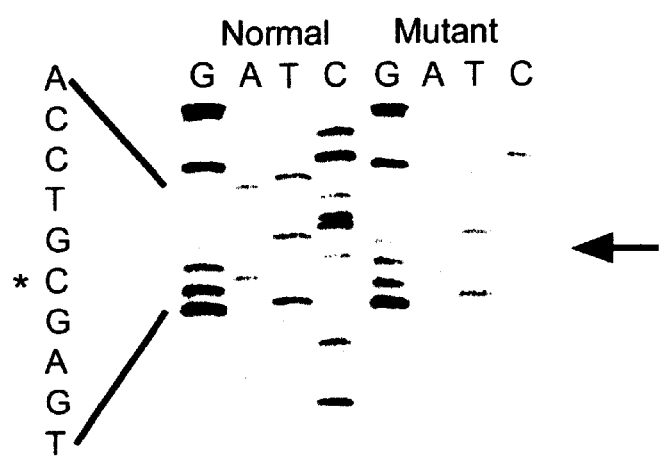

Sequence comparison identified two different mutations in the cystatin B gene in this group of affected individuals. One is a G to C transversion mutation at the last nucleotide of intron 1 (SEQ ID NO:10), altering the sequence of the 3' splice site AG dinucleotide that appears in this position in almost all introns (FIGS. 3 (SEQ ID NO:1) and 4A). The second mutation, which was found in alleles of the cystatin B gene from two of the four families, changes CGA to TGA, thus generating a translation stop codon, at amino acid position 68 (SEQ ID NO:11) (FIGS. 3 and 4B).

Example 4

Screening of Individuals for EPM1

Figure 4C:
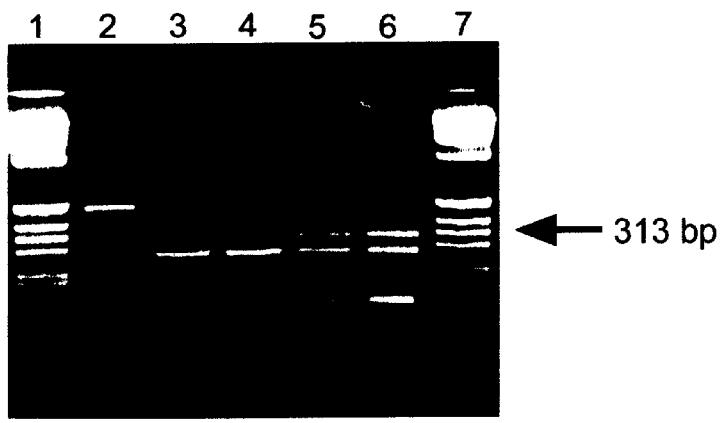

The 3' splice mutation destroys a recognition site for the restriction enzyme BfaI, which allowed us to develop a simple test to screen alleles in large numbers of unaffected individuals (FIG. 4C). The 3' splice site mutation was screened in the general population in 95 unrelated Americans (190 chromosomes), 90% of whom were of European ancestry and 10% with other ethnic backgrounds. The stop codon mutation was screened in 70 Finnish EPM1 carrier parents. We found no mutant alleles after screening 190 chromosomes for this change in 95 unrelated, unaffected individuals. All 70 Finnish individuals contained the common ancestral haplotype around the EPM1 locus on one of their chromosomes. To distinguish mutations from polymorphisms, only the non-ancestral haplotype chromosome of these individuals was considered. DNA from these individuals was PCR-amplified and the products were directly sequenced by using the AmpliCycleTM Sequencing Kit (Perkin Elmer, U.S.A.). Direct sequencing of PCR products to screen 70 alleles for the stop codon mutation in the cystatin B gene from unaffected control individuals found no mutant alleles in this sample. Therefore two mutations that reduce expression of the protein in EPM1 patients are not observed in the general populace.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing rom the spirit or scope of the appended claims.

What is claimed is:

1. A pair of isolated nucleic acid molecules, each from about 10 to 200 nucleotides in length, the first nucleic acid molecule of said pair comprising a sequence of at least 10 contiguous nucleotides having 100% sequence identity to the nucleic acid sequence set forth in SEQ ID NO:1 and the second nucleic acid molecule of said pair comprising a sequence of at least 10 contiguous nucleotides having 100% sequence identity to the reverse complement of the nucleic acid sequence set forth in SEQ ID NO:1, wherein said sequence of said second nucleic acid molecule is located 3' of the nucleic acid sequence of the first nucleic acid molecule in SEQ ID NO:1.

2. The pair of claim 1, wherein the nucleic acid sequences of said first and second nucleic acid molecules are located 5' and 3', respectively, of the region of SEQ ID NO:1 corresponding to the location of a mutation associated with epilepsy.

3. The pair of claim 2, wherein said mutation is a mutation at position 1924 of SEQ ID NO:1.

4. The pair of claim 2, wherein said mutation is a mutation at position 2387 of SEQ ID NO: 1.

5. The pair according to claim 1, wherein said pair of nucleic acid molecules primes amplification of a portion of a human cystatin B nucleic acid molecule comprising a nucleotide position corresponding to a mutation associated with epilepsy when used in a polymerase chain reaction with a human cystatin B nucleic acid molecule as a template.

* * * * *

SEQUENCE LISTING

<160> NUMBER OF SEQ ID NOS: 11

<210> SEQ ID NO 1
<211> LENGTH: 2822
<212> TYPE: DNA
<213> ORGANISM: Homo sapiens

<400> SEQUENCE: 1

| | | | | | |
|---|---|---|---|---|---|
| ctgcaggatt | gccoctactc | cgactgcccc | ttccctatcg | tcccaccctg | cgcgcccaac | 60 |
| ccaccggcga | cacccggccg | cgcccccgcc | ccggtccgtg | tgactcggcg | cccggaaaga | 120 |
| cgataccagc | cccgggaggg | gggcgctccc | tcccgacacc | agcgctgggc | gcggagaccc | 180 |
| agcctgcggc | gagtggtggc | caggctcccc | gccccgcgcc | ccgcccgcg | cccgccccg | 240 |
| cgcgtccctt | cttgcgggc | caccgcgacc | cgcagggga | ctccgaagcc | aaagtgcctc | 300 |
| ctccccgccc | cttggttccg | cccgcgcgtc | acgtgacccc | agcgcctact | tgggctgagg | 360 |
| agccgccgcg | tccctcgcc | gagtcccctc | gccagattcc | ctccgtcgcc | gccaagatga | 420 |
| tgtgcgggc | gccctccgcc | acgcagccgg | ccaccgccga | gacccagcac | atcgccgacc | 480 |
| aggtgggtgg | gccgcgggga | cggggccggc | ccggagtcct | gccttagcct | cagggcgcgg | 540 |
| ccgcggctcc | tggagcgaaa | gaagccgctt | tggccccgct | cgcacccct | gggctggccc | 600 |
| gggctgtggc | cgtgagaggc | ctccctccgc | tcgggtcgcg | cgcgagtgag | cagcgggggg | 660 |
| ccgcgcctgg | ggcgccgctg | gggagacatt | gggctccgct | gaatacagca | agggcgagtg | 720 |
| ggaattgata | gcccggagca | gggtgcggtc | cctgcatgga | cagtctctga | gaggaaaccc | 780 |
| cagggatgag | gcgcttctgg | tttcaggcag | gcagggtgat | cgggcgtcgc | cggcgatggc | 840 |
| gcaggtgagc | agccggctcc | gatctccacg | gtgatccgat | agcaagcggg | tgggaagggt | 900 |
| ctggctaaac | tgacttagcc | aggcttcttg | ctaaaagtgg | attttacaag | gaagtgcgca | 960 |
| ggtggcctag | gcgcttcagg | agcccgacta | cagtttggcc | aagcaagaat | ctttgtcaat | 1020 |
| atcctcatct | agttcgggaa | aaaaatcatg | agagagagtg | caagaggtcc | ccagtgataa | 1080 |
| ggcacatggg | ttaaaaactt | aagtgtatct | gcataaaagg | tccacaggtt | tctttacatg | 1140 |
| cttccgattc | tagcactgtt | tcaaactgta | agtctaaata | aaagttaaa | acacagaaaa | 1200 |
| acaagataaa | aaccgggctg | ggttgcagat | ggcaactttc | cctgtgtctc | ggtttcctcg | 1260 |
| tctgtaaaat | ggacgtcctg | ttgctctgcg | cctgccagaa | gattctggag | gggctgaaat | 1320 |
| gagcaggtca | tctgtgcaag | aagcccctc | cggtggagca | caggccaggc | ccgcctcgct | 1380 |
| gtcatggttg | gtgaccgacg | ggatgcccca | agcaagaaca | ggtccaggcg | atgctgaggc | 1440 |
| ctgtgttttt | ttttttgtt | tttgagactc | agtctcaact | cttgcccagg | gtggagtgca | 1500 |
| gtggcacaat | ctcggcccac | tgcaacctcc | gcttcccagg | ttcaagggat | tctcctgcct | 1560 |
| tagcctcccg | agtagctggg | attgcaggtg | ctcgccacca | cgcccagcta | attttgtat | 1620 |
| ttttagtaga | aacggggttt | tgccatttgg | ctaggctggt | ctcaaactcc | tgacctcaag | 1680 |
| tgatccgccc | acctcagcct | cccaaagttc | tgggattaca | tccttgagcc | accgtaccca | 1740 |
| gctggaactg | ttttttttcta | ctttattatt | aggctgacag | tttaaatgtc | ccttcagttg | 1800 |
| taagagacaa | ttgtgtgaag | agccagtgtc | agaatcgtgt | gtgtgctcac | atgcgtgcaa | 1860 |
| gttactctag | caggagggaa | tccaagaagc | cactgagaca | tcctcattct | gtcccttctg | 1920 |
| tctaggtgag | gtcccagctt | gaagagaaag | aaaacaagaa | gttccctgtg | tttaaggccg | 1980 |
| tgtcattcaa | gagccaggtg | gtcgcgggga | caaactactt | catcaaggta | gagtgtgggc | 2040 |

```
ctcaggaggg cctgccccga acgggtgctg gtaggaaacc gcctgtgcag gcccgggctg     2100
tgtggtctta ggtgctgggg cgccctgtgg ctgcccctg agataagcat cctactgtgt      2160
gtgtccatcg gcctttcagg aggactaggg cttctgggga gctaagaacc ccaaggaaac    2220
aagtgtggga tgtgaggcat cccctgcaca tgcaggagaa gacaagattg tcttcagctg   2280
gctgctaatg acctggaggg cgcagcaag gtgacttggg atcagaggct tcgctcactc    2340
cgctctcttc ccaggtgcac gtcggcgacg aggacttcgt acacctgcga gtgttccaat   2400
ctctccctca tgaaaacaag cccttgacct tatctaacta ccagaccaac aaagccaagc   2460
atgatgagct gacctatttc tgatcctgac tttggacaag gcccttcagc cagaagactg   2520
acaaagtcat cctccgtcta ccagagcgtg cacttgtgat cctaaaataa gcttcatctc   2580
cgctgtgccc ttggggtgga aggggcagga ttctgcagct gcttttgcat ttctcttcct   2640
aaatttcatt gtgttgattt ctttccttcc caataggtga tcttaattac tttcagaata   2700
ttttcaaaat agatatattt ttaaaatcct tacagattgc ctcctttgct tttagacttt   2760
tttcttgctg ctaaccaccc cgggcaggtc cttcccctcc aggcaggagg gcggagagag   2820
tc                                                                   2822

<210> SEQ ID NO 2
<211> LENGTH: 98
<212> TYPE: PRT
<213> ORGANISM: Homo sapiens

<400> SEQUENCE: 2

Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Glu Asn
            20                  25                  30

Lys Lys Phe Pro Val Phe Lys Ala Val Ser Phe Lys Ser Gln Val Val
        35                  40                  45

Ala Gly Thr Asn Tyr Phe Ile Lys Val His Val Gly Asp Glu Asp Phe
    50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe

<210> SEQ ID NO 3
<211> LENGTH: 21
<212> TYPE: DNA
<213> ORGANISM: Homo sapiens

<400> SEQUENCE: 3
ctccgactgc cccttcccta t                                              21

<210> SEQ ID NO 4
<211> LENGTH: 24
<212> TYPE: DNA
<213> ORGANISM: Homo sapiens

<400> SEQUENCE: 4
gagacacagg gaaagttgcc atct                                           24

<210> SEQ ID NO 5
<211> LENGTH: 23
```

-continued

```
<212> TYPE: DNA
<213> ORGANISM: Homo sapiens

<400> SEQUENCE: 5
ccaccgtacc cagctggaac tgt                                              23

<210> SEQ ID NO 6
<211> LENGTH: 24
<212> TYPE: DNA
<213> ORGANISM: Homo sapiens

<400> SEQUENCE: 6
cggaggatga ctttgtcagt cttc                                             24

<210> SEQ ID NO 7
<211> LENGTH: 24
<212> TYPE: DNA
<213> ORGANISM: Homo sapiens

<400> SEQUENCE: 7
taaggccgtg tcattcaaga gcca                                             24

<210> SEQ ID NO 8
<211> LENGTH: 19
<212> TYPE: DNA
<213> ORGANISM: Homo sapiens

<400> SEQUENCE: 8
cgccgagacc cagcacatc                                                   19

<210> SEQ ID NO 9
<211> LENGTH: 24
<212> TYPE: DNA
<213> ORGANISM: Homo sapiens

<400> SEQUENCE: 9
tcttagctcc ccagaagccc tagt                                             24

<210> SEQ ID NO 10
<211> LENGTH: 2822
<212> TYPE: DNA
<213> ORGANISM: Homo sapiens

<400> SEQUENCE: 10
ctgcaggatt gccctactc cgactgcccc ttccctatcg tcccaccctg cgcgcccaac        60
ccaccggcga cacccggccg cgccccgcc ccggtccgtg tgactcggcg cccggaaaga       120
cgataccagc cccgggaggg gggcgctccc tcccgacacc agcgctgggc gcggagaccc      180
agcctgcggc gagtggtggc caggctcccc gcccgcgcc ccgccccgcg ccccgccccg       240
cgcgtccctt cttgcggggc caccgcgacc cgcaggggga ctccgaagcc aaagtgcctc      300
ctccccgccc cttggttccg cccgcgcgtc acgtgacccc agcgcctact tgggctgagg      360
agccgccgcg tccctcgcc gagtccctc gccagattcc ctccgtcgcc gccaagatga       420 tgtgcgggc gccctccgcc acgcagccgg ccaccgccga cccagcac atcgccgacc        480 aggtgggtgg gccgcgggga cggggccggc ccggagtcct gccttagcct cagggcgcgg      540
ccgcggctcc tggagcgaaa gaagccgctt tggccccgct gcgcacccct gggctggccc      600
gggctgtggc cgtgagaggc ctccctccgc tcgggtcgcg cgcgagtgag cagcgggggg     660
ccgcgcctgg ggcgccgctg gggagacatt gggctccgct gaatacagca agggcgagtg    720
```

```
ggaattgata gcccggagca gggtgcggtc cctgcatgga cagtctctga gaggaaaccc    780
cagggatgag gcgcttctgg tttcaggcag gcagggtgat cgggcgtcgc cggcgatggc    840
gcaggtgagc agccggctcc gatctccacg gtgatccgat agcaagcggg tgggaagggt    900
ctggctaaac tgacttagcc aggcttcttg ctaaaagtgg attttacaag gaagtgcgca    960
ggtggcctag gcgcttcagg agcccgacta cagtttggcc aagcaagaat ctttgtcaat   1020
atcctcatct agttcgggaa aaaatcatg agagagagtg caagaggtcc ccagtgataa   1080
ggcacatggg ttaaaaactt aagtgtatct gcataaaagg tccacaggtt tctttacatg   1140
cttccgattc tagcactgtt tcaaactgta agtctaaata aaaagttaaa acacagaaaa   1200
acaagataaa aaccgggctg ggttgcagat ggcaactttc cctgtgtctc ggtttcctcg   1260
tctgtaaaat ggacgtcctg ttgctctgcg cctgccagaa gattctggag gggctgaaat   1320
gagcaggtca tctgtgcaag aagcccctc cggtggagca caggccaggc ccgcctcgct   1380
gtcatggttg gtgaccgacg ggatgcccca agcaagaaca ggtccaggcg atgctgaggc   1440
ctgtgttttt ttttttgtt tttgagactc agtctcaact cttgcccagg gtggagtgca   1500
gtggcacaat ctcggcccac tgcaacctcc gcttcccagg ttcaagggat tctcctgcct   1560
tagcctcccg agtagctggg attgcaggtg ctcgccacca cgcccagcta attttgtat    1620
ttttagtaga acgggtttt tgccatttgg ctaggctggt ctcaaactcc tgacctcaag   1680
tgatccgccc acctcagcct cccaaagttc tgggattaca tccttgagcc accgtaccca   1740
gctggaactg ttttttcta ctttattatt aggctgacag tttaaatgtc ccttcagttg    1800
taagagacaa ttgtgtgaag agccagtgtc agaatcgtgt gtgtgctcac atgcgtgcaa   1860
gttactctag caggagggaa tccaagaagc cactgagaca tcctcattct gtcccttctg   1920
tctacgtgag gtcccagctt gaagagaaag aaaacaagaa gttccctgtg tttaaggccg   1980
tgtcattcaa gagccaggtg gtcgcgggga caaactactt catcaaggta gagtgtgggc   2040
ctcaggaggg cctgccccga acgggtgctg gtaggaaacc gcctgtgcag gcccgggctg   2100
tgtggtctta ggtgctgggg cgccctgtgg ctgcccctg agataagcat cctactgtgt    2160
gtgtccatcg gccttcagg aggactaggg cttctgggga gctaagaacc ccaaggaaac    2220
aagtgtggga tgtgaggcat cccctgcaca tgcaggagaa gacaagattg tcttcagctg   2280
gctgctaatg acctggaggg gcgcagcaag gtgacttggg atcagaggct tcgctcactc   2340
cgctctcttc ccaggtgcac gtcggcgacg aggacttcgt acacctgcga gtgttccaat   2400
ctctccctca tgaaaacaag cccttgacct tatctaacta ccagaccaac aaagccaagc   2460
atgatgagct gacctatttc tgatcctgac tttggacaag gcccttcagc cagaagactg   2520
acaaagtcat cctccgtcta ccagagcgtg cacttgtgat cctaaaataa gcttcatctc   2580
cgctgtgccc ttggggtgga aggggcagga ttctgcagct gcttttgcat ttctcttcct   2640
aaatttcatt gtgttgattt ctttccttcc caataggtga tcttaattac tttcagaata   2700
ttttcaaaat agatatattt ttaaaatcct tacagattgc ctccttttgct tttagacttt   2760
tttcttgctg ctaaccaccc cgggcaggtc cttcccctcc aggcaggagg gcggagagag   2820
tc                                                                   2822
```

<210> SEQ ID NO 11
<211> LENGTH: 2822
<212> TYPE: DNA
<213> ORGANISM: Homo sapiens

```
<400> SEQUENCE: 11
ctgcaggatt gccctactc cgactgcccc ttccctatcg tcccaccctg cgcgcccaac      60
ccaccggcga cacccggccg cgccccgcc ccggtccgtg tgactcggcg cccggaaaga    120
cgataccagc cccgggaggg gggcgctccc tcccgacacc agcgctgggc gcggagaccc    180
agcctgcggc gagtggtggc caggctcccc gccccgcgcc ccgccccgcg ccccgcccccg    240 cgcgtccctt cttgcggggc caccgcgacc ccgcagggga ctccgaagcc aaagtgcctc    300
ctccccgccc cttggttccg cccgcgcgtc acgtgacccc agcgcctact tgggctgagg    360
agccgccgcg tcccctcgcc gagtcccctc gccagattcc ctccgtcgcc gccaagatga    420
tgtgcggggc ccctccgcc acgcagccgg ccaccgccga acccagcac atcgccgacc    480 aggtgggtgg gccgcgggga cggggccggc ccggagtcct gccttagcct cagggcgcgg    540
ccgcggctcc tggagcgaaa gaagccgctt tggccccgct gcgcacccct gggctggccc    600
gggctgtggc cgtgagaggc ctccctccgc tcgggtcgcg cgcgagtgag cagcgggggg    660
ccgcgcctgg ggcgccgctg gggagacatt gggctccgct gaatacagca agggcgagtg    720
ggaattgata gcccggagca gggtgcggtc cctgcatgga cagtctctga gaggaaaccc    780
cagggatgag gcgcttctgg tttcaggcag gcagggtgat cgggcgtcgc cggcgatggc    840
gcaggtgagc agccggctcc gatctccacg gtgatccgat agcaagcggg tgggaagggt    900
ctggctaaac tgacttagcc aggcttcttg ctaaaagtgg attttacaag gaagtgcgca    960
ggtggcctag gcgcttcagg agcccgacta cagtttggcc aagcaagaat ctttgtcaat   1020
atcctcatct agttcgggaa aaaaatcatg agagagagtg caagaggtcc ccagtgataa   1080
ggcacatggg ttaaaaactt aagtgtatct gcataaaagg tccacaggtt tctttacatg   1140
cttccgattc tagcactgtt tcaaactgta agtctaaata aaaagttaaa acacagaaaa   1200
acaagataaa aacgggctg ggttgcagat ggcaactttc cctgtgtctc ggtttcctcg   1260
tctgtaaaat ggacgtcctg ttgctctgcg cctgccagaa gattctggag gggctgaaat   1320
gagcaggtca tctgtgcaag aagcccctc cggtggagca caggccaggc ccgcctcgct   1380
gtcatggttg gtgaccgacg ggatgcccca agcaagaaca ggtccaggcg atgctgaggc   1440
ctgtgttttt ttttttttgtt tttgagactc agtctcaact cttgcccagg gtggagtgca   1500
gtggcacaat ctcggcccac tgcaacctcc gcttcccagg ttcaagggat tctcctgcct   1560
tagcctcccg agtagctggg attgcaggtg ctcgccacca cgcccagcta attttttgtat   1620 ttttagtaga acgggggttt tgccatttgg ctaggctggt ctcaaactcc tgacctcaag   1680
tgatccgccc acctcagcct cccaaagttc tgggattaca tccttgagcc accgtaccca   1740
gctggaactg ttttttttcta ctttattatt aggctgacag tttaaatgtc ccttcagttg   1800
taagagacaa ttgtgtgaag agccagtgtc agaatcgtgt gtgtgctcac atgcgtgcaa   1860
gttactctag caggagggaa tccaagaagc cactgagaca tcctcattct gtcccttctg   1920
tctaggtgag gtcccagctt gaagagaaag aaaacaagaa gttccctgtg tttaaggccg   1980
tgtcattcaa gagccaggtg gtcgcgggga caaactactt catcaaggta gagtgtgggc   2040
ctcaggaggc cctgccccga acgggtgctg gtaggaaacc gcctgtgcag gcccgggctg   2100
tgtggtctta ggtgctgggg cgccctgtgg ctgccccctg agataagcat cctactgtgt   2160
gtgtccatcg gcctttcagg aggactaggg cttctgggga gctaagaacc ccaaggaaac   2220
aagtgtggga tgtgaggcat cccctgcaca tgcaggagaa gacaagattg tcttcagctg   2280
gctgctaatg acctggaggg gcgcagcaag gtgacttggg atcagaggct tcgctcactc   2340
```

-continued

```
cgctctcttc ccaggtgcac gtcggcgacg aggacttcgt acacctgtga gtgttccaat    2400
ctctccctca tgaaaacaag cccttgacct tatctaacta ccagaccaac aaagccaagc    2460
atgatgagct gacctatttc tgatcctgac tttggacaag gcccttcagc cagaagactg    2520
acaaagtcat cctccgtcta ccagagcgtg cacttgtgat cctaaaataa gcttcatctc    2580
cgctgtgccc ttggggtgga aggggcagga ttctgcagct gcttttgcat ttctcttcct    2640
aaatttcatt gtgttgattt ctttccttcc caataggtga tcttaattac tttcagaata    2700
ttttcaaaat agatatattt ttaaaatcct tacagattgc ctcctttgct tttagactt    2760 tttcttgctg ctaaccaccc cgggcaggtc cttcccctcc aggcaggagg gcggagagag    2820
tc                                                                    2822
```